United States Patent [19]

Yamaki

[11] Patent Number: 4,762,955
[45] Date of Patent: Aug. 9, 1988

[54] PROCESS FOR SEPARATING PARA-DICHLOROBENZENE FROM ISOMERIC MIXTURE OF DICHLOROBENZENES

[75] Inventor: Shigetoshi Yamaki, Iwaki, Japan

[73] Assignee: Kureha Kagaku Kogyo Kabushiki Kaisha, Nihonbashi, Japan

[21] Appl. No.: 863,601

[22] Filed: May 15, 1986

[30] Foreign Application Priority Data

May 23, 1985 [JP] Japan .................. 60-111261

[51] Int. Cl.$^4$ .................. C07C 17/38; C07C 25/08
[52] U.S. Cl. .................................... 570/211
[58] Field of Search ........................... 570/211

[56] References Cited

U.S. PATENT DOCUMENTS

| | | | |
|---|---|---|---|
| 2,835,707 | 5/1958 | Stoesser et al. | 570/211 |
| 3,557,226 | 1/1971 | Sherk | 570/211 |
| 4,300,004 | 11/1981 | Wissner et al. | 570/211 |

FOREIGN PATENT DOCUMENTS 2855940 12/1979 Fed. Rep. of Germany ...... 570/211

OTHER PUBLICATIONS

Campbell et al, JACS, 70, 553–561 (1948).
Wibaut et al, Rec. Trav. Chim., 56, 65–70 (1937).
Chemical Abstracts 89: 197137s.

Primary Examiner—J. E. Evans
Attorney, Agent, or Firm—Weiser & Stapler

[57] ABSTRACT

Disclosed herein is a process for separating p-dichlorobenzene from an isomeric mixture of dichlorobenzenes comprising adding 1-bromo-4-chlorobenzene, 1,4-dibromobenzene or a mixture of 1-bromo-4-chlorobenzene and 1,4-dibromobenzene to the isomeric mixture of dichlorobenzenes, heating the thus formed mixture to dissolve a part or the whole thereof, cooling the thus treated material, thereby crystallizing the eutictic crystals of p-dichlorobenzene and 1-bromo-4-chlorobenzene or 1,4-dibromobenzene or the eutectic crystals of p-dichlorobenzene, 1-bromo-4-chlorobenzene and 1,4-dibromobenzene, and thus separating p-dichlorobenzene from the isomeric mixture of dichlorobenzenes.

15 Claims, 1 Drawing Sheet

PROCESS FOR SEPARATING PARA-DICHLOROBENZENE FROM ISOMERIC MIXTURE OF DICHLOROBENZENES

BACKGROUND OF THE INVENTION

The present invention relates to a process for separating (removing) p-dichlorobenzene (hereinafter referred to as p-DCB) from an isomeric mixture of dichlorobenzenes, and particularly to a process for separating (removing) p-DCB from a mixture of m-dichlorobenzene (hereinafter referred to as m-DCB) and p-DCB. More in detail, the present invention relates to a process for separating (removing) p-dichlorobenzene from an isomeric mixture of dichlorobenzenes, comprising adding an eutectic agent of 1-bromo-4-chlorobenzene (hereinafter referred to as BCB), 1,4-dibromobenzene (hereinafter referred to as DBB) or a mixture of BCB and DBB to the isomeric mixture, heating the thus formed mixture to dissolve thereof partly or wholly, and cooling the thus formed solution, thereby crystallizing eutectic crystals (co-crystals) of p-DCB and the eutectic agent in order to separate p-DCB from the isomeric mixture of dichlorobenzenes.

The process according to the present invention is particularly useful industrially as a process for economically separating p-DCB from a mixture of m-DCB and p-DCB to obtain highly pure m-DCB (purity: higher than 95%).

The isomeric mixture of dichlorobenzenes is obtained by chlorinating benzene or monochlorobenzene. The composition of the isomeric mixture of dichlorobenzenes depends largely on the kinds of the catalyst and the reaction conditions of chlorination, however, in ordinary cases, the mixture consists essentially of from 55 to 80 % by weight of p-DCB, from 0.01 to 1% by weight of m-DCB and from 20 to 45% by weight of o-dichlorobenzene (hereinafter referred to o-DCB).

By cooling the reaction product to from $-20°$ to $10°$ C., most of p-DCB therein crystals out therefrom, and by filtering the thus obtained crystalline slurry, most of p-DCB is removed to obtain crude o-DCB consisting essentially of from 60 to 85% by weight of o-DCB, from 15 to 40% by weight of p-DCB and from 0.02 to 2% by weight of m-DCB. The above-mentioned steps have been ordinarily carried out industrially.

By distilling most of p-DCB and m-DCB off from the thus obtained crude o-DCB, purified o-DCB consisting essentially of from 80 to 99% by weight, from 0.1 to 20% by weight of p-DCB and from 0 to 1% by weight of m-DCB is obtained. The step have been also actually carried out industrially.

By isomerizing the isomeric mixture of dichlorobenzenes, p-DCB, crude o-DCB, purified o-DCB and the like in the presence of a catalyst mainly composed of anhydrous aluminum chloride, an isomeric mixture of dichlorobenzenes rich in m-DCB (from 40 to 60% by weight of m-DCB, from 20 to 30% by weight of p-DCB and from 10 to 30% by weight of o-DCB) is obtained, and by distilling o-DCB off from the isomeric mixture, crude m-DCB consisting essentially of from 55 to 70% by weight of m-DCB, from 30 to 45% by weight of p-DCB and from 0 to 3% by weight of o-DCB is obtained (refer to G. A. Olah et al., J. Org. Chem., 27, 3449–3455 (1962) and U.S. Pat. No. 3,170,961).

The isomeric mixture of dichlorobenzenes according to the present invention is the above-mentioned crude o-DCB, purified o-DCB and crude m-DCB. According to the process of the present invention, purified o-DCB containing a smaller amount of p-DCB is obtained from the crude o-DCB or the purified o-DCB, and a highly pure m-DCB is obtained from the crude m-DCB.

Various processes have been proposed as the process for removing p-DCB from the crude m-DCB to obtain a highly pure m-DCB, however, every one of them uses a large amount of chemicals and separating agents, or consumes a large amount of energy and accordingly, the industrial value thereof is quite low. For instance, in the process by which the crystallization through deep cooling and the accurate distillation are used in combination (refer to DE-OS No. 2855940), crude m-DCB is cooled to a temperature of $-30°$ C. lower than the melting point of m-DCB ($-24°$ C.), thereby crystallizing the eutectic crystals of m-DCB and p-DCB, and thus removing p-DCB, then the still-remaining p-DCB is removed by the accurate distillation. However, since the difference of the boiling point of p-DCB (174.1° C.) and that of m-DCB (173.0° C.) is very small, a large amount of energy is necessary for carrying out the accurate distillation.

In the process of utilizing the property that only m-DCB is selectively sulfonated in the case of subjecting crude m-DCB to sulfonation by sulfuric acid (refer to Japanese patent publication No. 57-4614/1982), a large amount of sulfuric acid is used and a large amount of energy is consumed for hydrolysis of the sulfonated product and for regeneration of the spent sulfuric acid.

In the process of utilizing the property that only m-DCB is brominated in the case of subjecting crude m-DCB to bromination (refer to U.S. Pat. No. 3,170,961/1965), a mixture of p-DCB and m-DCB, the difference between the boiling point of (p-DCB) and that of m-DCB being small, is brominated to convert the mixture into the mixture of p-DCB (boiling point: 92° C./58 mmHg) and 1-bromo-2,4-dichlorobenzene (boiling point: 141°–142° C./58 mmHg), and the thus treated mixture is distilled to remove p-DCB and 1-bromo-2,4-dichlorobenzene is reduced to m-DCB by hydrogen. However, the process is not economical because of the consumption of a large amount of expensive bromine.

In the extracting distillation process (refer to Japanese patent application Laying-Open (KOKAI) Nos. 50-19722/1975, 54-160322/1979, and 58-174336/1983, since an expensive extracting solvent such as hexamethylphophorotriamide, sulforane, alkylaniline, dimethylimidazolidinone, etc. is used, not only there are problems concerning the safety and the stability but also the separating performance is not sufficient and a large amount of energy is necessary.

In the process of removing p-DCB by adsorption on zeolite (refer to Japanese patent applications Laying-Open (KOKAI) No. 52-62229/1977, No. 58-131924/1983 and No. 58-150524/1983), the performance of zeolite in separating p-DCB from the mixture of p-DCB and m-DCB is not sufficient and a large amount of zeolite is necessary. In addition, a large amount of a solvent is necessary for desorbing the adsorbed material and a large amount of energy is consumed for recovering the solvent.

Although it has been known that (1) p-DCB and BCB, (2) p-DCB and DBB and (3) p-DCB and BCB plus DBB respectively form the eutectic crystals or the solid solution (refer to A. N. Cambell et al.; J. Am. Chem. Soc., 70, 553–561 (1948)), there have not been proposed to separate p-DCB from the isomeric mixture of dichlorobenzenes while utilizing the property of p-DCB in forming the eutectic crystals with BCB, etc.

As a result of the present inventors' studing on the solid-liquid equilibrium relationship of (1) p-DCB and BCB, (2) p-DCB and DBB and (3) p-DCB and BCB plus DBB in the solvent (m-DCB and o-DCB), it has been found that in the case of adding BCB, DBB or a mixture of BCB and DBB to the isomeric mixture of dichlorobenzenes and cooling the thus formed mixture, p-DCB is crystallized as the eutectic crystals with BCB, DBB or mixture of BCB and DBB, and the present inventors have attained the present invention based on the above-mentioned findings.

SUMMARY OF THE INVENTION

In an aspect of the present invention, provided there is a process for separating p-DCB from an isomeric mixture of dichlorobenzenes, comprising adding 1-bromo-4-chlorobenzene (BCB), 1,4-dibromobenzene (DBB) or a mixture of BCB and DBB to an isomeric mixture of dichlorobenzenes, dissolving a part or the whole thereof by heating the thus formed mixture, cooling the thus formed solution, thereby crystallizing p-DCB as eutectic crystals with BCB, DBB or the mixture of BCB and DBB.

BRIEF DESCRIPTION OF THE DRAWING

Of the attached drawing.

DETAILED DESCRIPTION OF THE INVENTION

Figure 1:
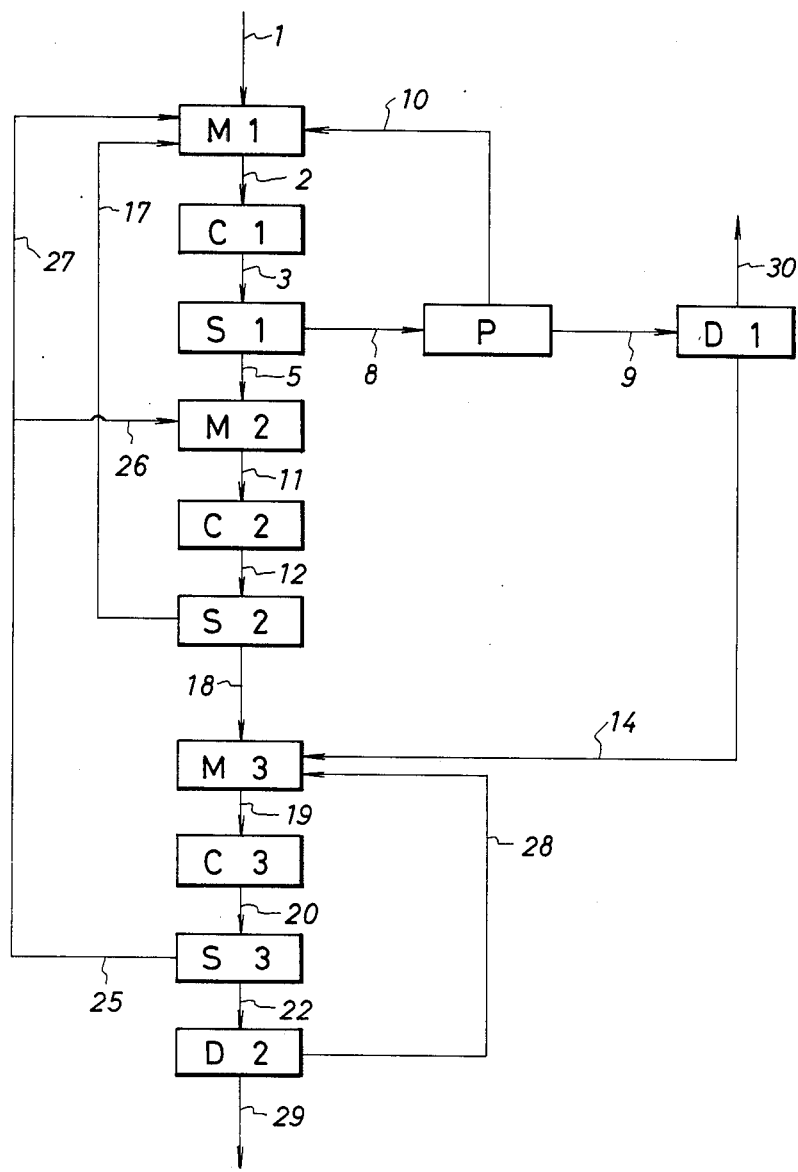
FIG. 1 is a flow chart of one of the examples of the process according to the present invention.

Although the isomeric mixture of dichlorobenzenes as a raw material of the present invention, is crude o-DCB, purified o-DCB and crude m-DCB which are easily producible industrially, there is no restriction regarding the ratio of m-DCB, p-DCB and o-DCB in the isomeric mixture of dichlorobenzenes in the actual enforcement of the present invention. In addition, although it is approved that the isomeric mixture of dichlorobenzenes contains a small amount of impurities such as monochlorobenzene, trichlorobenzene, etc., it is preferable to have removed such impurities in advance. Futhermore, BCB and/or DBB may be contained in the isomeric mixture of dichlorobenzenes.

It is not necessary that BCB and/or DBB which are added for forming the eutectic crystals (co-crystals) are pure substances, and BCB and/or DBB may contain dichlorobenzenes. In addition, the mixing ratio of BCB and DCB in the mixture thereof is not particularly limited.

BCB, DCB and mixtures thereof (referred to as the "eutectic agent") may be liquid or solid.

The amount of the eutectic agent used according to the present invention is from 10 to 200 parts, preferably from 50 to 150 parts by weight to 100 parts by weight of the isomeric mixture of dichlorobenzenes, and from 0.5 to 200 parts, preferably from 1 to 100 parts by weight to 1 part by weight of p-DCB in the isomeric mixture of dichlorobenzenes. It is preferable to heat the formed mixture of the eutectic agent and the isomeric mixture after adding the eutectic agent to the isomeric mixture and dissolve the isomeric mixture in the eutectic agent for making a uniform solution, however, the following step of crystallizing may be carried out even in the case of obtaining a partly undissolved material.

Crystallization of the eutectic crystals may be carried out at a temperature of lower than 30° C. at which the whole material does not solidify, and in the case where the isomeric mixture is composed mainly of m-DCB, the temperature is preferably from −25° to 10° C., and in the case where the isomeric mixture is composed mainly of o-DCB, the temperature is preferably from −20° to 10° C.

The apparatus used for crystallizing the eutectic crystals according to the present invention may be that which has been publicly known, and may be continuous type or batch type.

As the index of the efficiency of separation of p-DCB by the crystallization of the eutectic crystals, the index "K" of the following formula is suitable.

$$K = A/B$$

wherein A is the ratio of the concentration of p-DCB in the mother liquor to the concentration of the eutectic agent in the mother liquor, and B is the ratio of the concentration of p-DCB in the eutectic crystals to the concentration of the eutectic agent in the eutectic crystals.

Although the efficiency of separation of p-DCB is higher as the value of K is smaller, K is in the range of from 1.2 to 2.5 in the case where the eutectic agent is BCB, K is from 3 to 7 in the case where the eutectic agent is DBB and in the case where the eutectic agent is a mixture of BCB and DBB, K is an intermediate value between the above-mentioned ranges.

The obtained slurry is separated into the mother liquor and the eutectic crystal by filtration.

In the case of necessary, the eutectic agent is again added to the thus separated mother liquor to carry out the operation of crystallization and separation, and the finally obtained mother liquor is subjected to distillation to separate into m-DCB or o-DCB containing small amount of p-DCB and the eutectic agent. In the above-mentioned distillation, it is not necessary to separate p-DCB (boiling point: 174.1° C.), m-DCB (boiling point: 173.0° C.) and o-DCB (boiling point: 180.4° C.) to each other, and they are separated from BCB (boiling point: 196.9° C.) or DBB (boiling point: 218.6° C.) for the purpose of the present invention. Accordingly, the necessary energy for the distillation is small enough.

After removing the mother liquor adhered to the thus separated crystals by using a commerciallized apparatus for purifying crystals [the most suitable apparatus being the KUREHA-type crystal purifying apparatus manufactured by Kureha Kagaku Kogyo K.K. (referred to as KCP)], p-DCB and the eutectic agent are removed from the thus treated crystals by distillation.

Since the difference between the boiling point of p-DCB and that of the eutectic agent is large, the energy for distillation is small.

In addition, in the case where the thus separated p-DCB by distillation is subjected to isomerization as the raw material for m-DCB, it is not always necessary to remove the adhered mother liquor from the crystals in the apparatus for purifying crystals.

In the case of repeating the crystallization, the mother liquor adhering to the crystals separated in the second stage and thereafter, and the crystals are used as the eutectic agent in the crystallization of the first stage.

BCB melting at 64.6° C. used according to the present invention as the eutectic agent can be produced easily and in a low cost by bromination of monochlorobenzene, and DBB (melting point: 87.3° C.) also used as the eutectic agent can be produced easily and at a low cost by bromination of benzene or monobromobenzene. Although they are used in circulation, they are not consumed because of their chemical and thermal stability.

The separation of p-DCB from the isomeric mixture of dichlorobenzenes according to the present invention is particularly useful industrially in the case where the highly pure m-DCB of the purity of higher than 99% is produced from the mixture of m-DCB and p-DCB which is easily produced industrially. One of the concrete enforcement process is explained by the flow chart shown in FIG. 1. In addition, FIG. 1 and the following explanation do not limit the present invention.

A mixture of 1000 parts by weight of m-DCB and 500 parts by weight of p-DCB is supplied every hour to the first dissolving step (M 1) through line 1 continuously. The mother liquor removed from the crystals in the step of purifying the crystals (P) is supplied to M 1 through line 10, the crystals separated in the second separating step (S 2) is supplied to M 1 through line 17, and a part of the crystals separated in the third separating step (S 3) is also supplied to the first dissolving step M 1 through line 27, continuously. The thus supplied crystals are heated with the thus supplied mother liquor to be a solution which is supplied to the first crystallization step (C 1) at a rate of about 3700 parts by weight through line 2, the composition of the solution being about 36% by weight of m-DCB, about 28% by weight of p-DCB and about 45% by weight of BCB.

The solution supplied to C 1 is subjected to crystallization of crystals at a temperature of from −10° to −5° C., and the thus formed slurry is supplied to the first separating step (S 1) through line 3. The crystals separated in S 1 by filtration is supplied to the step P through line 8, and after removing the adhered mother liquor therein, the thus treated crystals are supplied to the first distilling step (D 1) through line 9. From the step D 1, the purified p-DCB (purity : 99.9%) is obtained at a rate of 490 parts by weight per hour through line 30.

The filtrate separated in the step S 1 is supplied to the second dissolving step (M 2) through line 5 and the larger part of the crystals separated in the step S 3 is supplied to the step M 2 through line 26 via the line 25, and the thus supplied materials are heated to be a solution and supplied to the second crystallizing step (C 2) through line 11, the composition of the solution being about 40% by weight of m-DCB, about 6% by weight of p-DCB and about 54% by weight of BCB.

The materials thus supplied to the step C 2 is subjected to crystallization therein at a temperature of from −20° to −15° C. and the thus formed slurry is supplied to the step S 2 through line 12. The filtrate separated in the step S 2 is supplied through line 18, BCB obtained in the step D 1 as the distillation bottom liquid is supplied as a liquid through line 14 and BCB obtained in the second distillation step (D 2) as the distillation bottom liquid is supplied through line 28, respectively to the third dissolving step (M 3), and they are heated to be a solution which is supplied to the third crystallizing step (C 3) through line 19, the composition of the solution being about 40% by weight of m-DCB, about 2.5% by weight of p-DCB and about 57% by weight of BCB. The solution is subjected to crystallization in the step C 3 at a temperature of from −25° to −20° C., and the thus formed slurry is supplied to the step S 3 through line 20. The filtrate separated in the step S 3 is supplied to the step D 2 through line 22. From the step D 2, m-DCB (purity: 99.1%) is obtained at a rate of 1009 parts by weight per hour as the top liquid of distillation through line 29.

The present invention will be explained more in detail while referring to the following non-limitative Examples.

EXAMPLE 1

To 650 g of an isomeric mixture of dichlorobenzenes of a composition of 38.8% by weight of p-DCB, 61.2% by weight of m-DCB and a trace of o-DCB, 350 g of BCB were added, and the mixture was heated to 50° C. to have a solution. By slowly cooling the solution to 1° C. while gently stirring thereof, crystals were crystallized in the solution. The thus obtained slurry was filtered by suction (a reduced pressure) to obtain 510 g of a filtrate of the composition of 13.8% by weight of p-DCB, 72.1% by weight of m-DCB, a trace of o-DCB and 14.1% by weight of BCB. The ratio of p-DCB to the total isomers of dichlorobenzenes was 16.1% by weight.

EXAMPLE 2

To 500 g of the filtrate obtained in Example 1, 359 g of BCB were added, and after treating the mixture as in Example 1, the mixture was subjected to crystallization at −20° C. to obtain 380 g of a filtrate of a composition of 3.3% by weight of p-DCB, 84.7% by weight of m-DCB, a trace of o-DCB and 12.0% by weight of BCB. The ratio of p-DCB to the total amount of the isomers of dichlorobenzenes was 3.7%.

EXAMPLE 3

To 360 g of the filtrate obtained in Example 2, 253 g of BCB were added, and after treating the mixture as in Example 1, the mixture was subjected to crystallization at −24° C. to obtain 320 g of a filtrate of a composition of 0.84% by weight of p-DCB, 87.2% by weight of m-DCB, a trace of o-DCB and 11.9% by weight of BCB. The ratio of the amount of p-DCB to the total amount of the isomers of dichlorobenzenes was 0.95% by weight.

EXAMPLES 4 to 32

While using BCB as the eutectic agent, in the same procedures as in Example 1, removal of p-DCB from the isomeric mixture of dichlorobenzenes under the various conditions shown in Table 1 was carried out. The results are also shown in Table 1. For reference, "% of p-DCB" is the ratio of p-DCB to the total amount of the isomers of dichlorobenzenes and "% of amount of filtrate" is the ratio of the amount of the filtrate obtained by filtration to the total amount of the supplied material by weight.

TABLE 1

| Example No. | Supply for crystallization Composition (%) | | | | | % of p-DCB | Temperature of crystallization (°C.) | Filtrate of the crystallization Composition (%) | | | | | % of p-DCB | Amount of filtrate (%) |
|---|---|---|---|---|---|---|---|---|---|---|---|---|---|---|
| | p-DCB | m-DCB | o-DCB | BCB | | | | p-DCB | m-DCB | o-DCB | BCB | | | |
| 4 | 25.25 | 39.50 | 0.25 | 35.00 | | 38.84 | 10 | 16.62 | 63.86 | 0.40 | 19.11 | | 20.55 | 58 |

TABLE 1-continued

| Example No. | Supply for crystallization Composition (%) | | | | % of p-DCB | Temperature of crystallization (°C.) | Filtrate of the crystallization Composition (%) | | | | % of p-DCB | Amount of filtrate (%) |
| --- | --- | --- | --- | --- | --- | --- | --- | --- | --- | --- | --- | --- |
| | p-DCB | m-DCB | o-DCB | BCB | | | p-DCB | m-DCB | o-DCB | BCB | | |
| 5 | 25.25 | 39.50 | 0.25 | 35.00 | 38.84 | −10 | 9.90 | 80.34 | 0.51 | 9.25 | 10.90 | 44 |
| 6 | 10.30 | 49.40 | 0.30 | 40.00 | 17.17 | 13 | 8.65 | 61.25 | 0.35 | 29.74 | 12.31 | 81 |
| 7 | 10.30 | 49.40 | 0.30 | 40.00 | 17.17 | 0 | 6.70 | 73.61 | 0.41 | 19.28 | 8.30 | 64 |
| 8 | 10.30 | 49.40 | 0.30 | 40.00 | 17.17 | −20 | 4.42 | 83.52 | 0.47 | 11.59 | 5.00 | 55 |
| 9 | 2.70 | 49.40 | 0.30 | 47.6 | 5.15 | −10 | 1.58 | 79.88 | 0.49 | 18.04 | 1.93 | 59 |
| 10 | 2.70 | 49.40 | 0.30 | 47.6 | 5.15 | −20 | 1.21 | 85.02 | 0.48 | 13.29 | 1.40 | 54 |
| 11 | 2.70 | 49.40 | 0.30 | 47.6 | 5.15 | −24 | 1.13 | 87.00 | 0.49 | 11.39 | 1.28 | 51 |
| 12 | 2.25 | 41.17 | 0.25 | 56.33 | 5.15 | 0 | 1.46 | 73.65 | 0.42 | 24.47 | 1.93 | 52 |
| 13 | 2.25 | 41.17 | 0.25 | 56.33 | 5.15 | −10 | 1.23 | 79.66 | 0.45 | 18.66 | 1.51 | 46 |
| 14 | 2.25 | 41.17 | 0.25 | 56.33 | 5.15 | −20 | 1.02 | 84.47 | 0.48 | 14.03 | 1.19 | 42 |
| 15 | 1.67 | 41.17 | 0.25 | 56.91 | 3.88 | 16 | 1.41 | 59.39 | 0.34 | 38.86 | 2.31 | 67 |
| 16 | 1.67 | 41.17 | 0.25 | 56.91 | 3.88 | 0 | 1.09 | 73.97 | 0.42 | 24.52 | 1.44 | 52 |
| 17 | 1.67 | 41.17 | 0.25 | 56.91 | 3.88 | −10 | 0.91 | 80.65 | 0.45 | 17.79 | 1.11 | 47 |
| 18 | 1.67 | 41.17 | 0.25 | 56.91 | 3.88 | −20 | 0.72 | 84.64 | 0.48 | 14.16 | 0.84 | 43 |
| 19 | 8.58 | 41.17 | 0.25 | 50.00 | 17.16 | 0 | 5.22 | 73.26 | 0.41 | 21.11 | 6.62 | 53 |
| 20 | 8.58 | 41.17 | 0.25 | 50.00 | 17.16 | −10 | 4.22 | 79.56 | 0.44 | 15.78 | 5.01 | 48 |
| 21 | 8.58 | 41.17 | 0.25 | 50.00 | 17.16 | −24 | 2.94 | 86.15 | 0.48 | 10.43 | 3.28 | 40 |
| 22 | 1.22 | 44.33 | 0.27 | 54.18 | 2.66 | 10 | 0.96 | 66.12 | 0.38 | 32.54 | 1.42 | 65 |
| 23 | 1.22 | 44.33 | 0.27 | 54.18 | 2.66 | −10 | 0.67 | 80.29 | 0.49 | 18.55 | 0.82 | 51 |
| 24 | 1.22 | 44.33 | 0.27 | 54.18 | 2.66 | −25 | 0.48 | 87.17 | 0.49 | 11.86 | 0.54 | 45 |
| 25 | 22.91 | 35.84 | 0.23 | 41.02 | 38.84 | 21 | 18.75 | 51.82 | 0.30 | 29.13 | 26.46 | 67 |
| 26 | 22.91 | 35.84 | 0.23 | 41.02 | 38.84 | 10 | 15.11 | 63.32 | 0.36 | 21.21 | 19.18 | 53 |
| 27 | 22.91 | 35.84 | 0.23 | 41.02 | 38.84 | 0 | 12.15 | 72.16 | 0.41 | 15.28 | 14.34 | 45 |
| 28 | 22.91 | 35.84 | 0.23 | 41.02 | 38.84 | −10 | 9.43 | 78.83 | 0.45 | 11.29 | 10.63 | 41 |
| 29 | 22.91 | 35.84 | 0.23 | 41.02 | 38.84 | −20 | 7.28 | 84.01 | 0.47 | 8.28 | 7.94 | 36 |
| 30 | 0.48 | 39.32 | 0.20 | 60.00 | 1.20 | 0 | 0.30 | 74.63 | 0.38 | 24.69 | 0.40 | 47 |
| 31 | 0.48 | 39.32 | 0.20 | 60.00 | 1.20 | −10 | 0.25 | 81.09 | 0.41 | 18.25 | 0.30 | 43 |
| 32 | 0.48 | 39.32 | 0.20 | 60.00 | 1.20 | −20 | 0.21 | 85.06 | 0.43 | 14.30 | 0.24 | 39 |

EXAMPLE 33

To 60 g of an isomeric mixture of dichlorobenzenes of a composition of 17.2% by weight of p-DCB, 82.3% by weight of m-DCB and 0.5% by weight of o-DCB, 40 g of DBB were added, and in the same manner as in Example 1, the operations were carried out and the mixture was subjected to crystallization at 0° C. to obtain 62 g of a filtrate of a composition of 9.31% by weight of p-DCB, 75.86% by weight of m-DCB, 0.46% by weight of o-DCB and 14.37% by weight of DBB. The ratio of the amount of p-DCB to the total amount of the isomers of dichlorobenzenes was 10.87% by weight.

EXAMPLE 34

To 120 g of an isomeric mixture of dichlorobenzenes of a composition of 17.2% by weight of p-DCB, 82.3% by weight of m-DCB and 0.5% by weight of o-DCB, 60 g of BCB and 40 g of DBB were added, and in the same manner as in Example 1, the operation was carried out and the mixture was subjected to crystallization at 0° C. to obtain 128 g of a filtrate of a composition of 6.69% by weight of p-DCB, 73.98% by weight of m-DCB, 0.44% by weight of o-DCB, 13.39% by weight of BCB and 5.50% by weight of DBB. The ratio of the amount of p-DCB to the total amount of the isomers of dichlorobenzene was 8.25% by weight.

What is claimed is:

1. A process for separating p-dichlorobenzene from an isomeric mixture of dichlorobenzenes, including m-dichlorobenzene, comprising adding 1-bromo-4-chlorobenzene, 1,4-dibromobenzene or a mixture of 1-bromo-4-chlorobenzene and 1,4-dibromobenzene, heating the thus formed mixture to dissolve a part or the whole of the solid material, cooling the thus obtained mixture to a temperature lower than 30° C., thereby crystallizing eutectic crystals consisting essentially of said 1-bromo-4-chlorobenzene and/or 1,4-dibromobenzene and p-dichlorobenzene, thus separating p-dichlorobenzene.

2. A process according to claim 1, wherein from 10 to 200 parts by weight of 1-bromo-4-chlorobenzene, 1,4-dibromobenzene or a mixture of 1-bromo-4-chlorobenzene and 1,4-dibromobenzene as an eutectic agent are added to 100 parts by weight of an isomeric mixture of dichlorobenzenes including m-dichlorobenzene so that the weight ratio of the amount of said eutectic agent to the amount of p-dichlorobenzene in said isomeric mixture of dichlorobenzenes is from 0.5 to 200.

3. A process according to claim 1, wherein 1-bromo-4-chlorobenzene is used as an eutectic agent.

4. A process according to claim 1, wherein 1,4-dibromobenzene is used as an eutectic agent.

5. A process according to claim 2, wherein from 50 to 150 parts by weight of the eutectic agent are added to 100 parts by weight of an isomeric mixture of dichlorobenzenes, including m-dichlorobenzene, so that the weight ratio of the amount of said eutectic agent to the amount of p-dichlorobenzene in said isomeric mixture of dichlorobenzene is from 1 to 100.

6. A process for separating p-dichlorobenzene from an isomeric mixture of dichlorobenzenes including m-dichlorobenzene which comprises:

adding to the isomeric mixture of dichlorobenzenes including m-dichlorobenzene an eutectic agent selected from the group consisting of 1-bromo-4-chlorobenzene, 1,4-dibromobenzenes or a mixture of, 1,4-dibromobenzene and 1-bromo-4-chlorobenzene, heating the formed mixture to dissolve a part or all of the solid material, cooling the formed mixture to a temperature lower than 30° C. and forming eutectic crystals consisting essentially of p-dichlorobenzene with the eutectic agent, and separating the eutectic crystals from the formed mixture thereby separating p-dichlorobenzene from the mixture.

7. The process of claim 6 wherein the isomeric mixture of dichlorobenzenes contains from 80 to 99% by weight of o-dichlorobenzene, from 0.1 to 20% by weight of p-dichlorobenzene and from 0.01% to 1% by weight of m-dichlorobenzene.

8. The process of claim 6 wherein the isomeric mixture of dichlorobenzenes contains from 20 to 45% by weight of o-dichlorobenzene, from 55 to 80% by weight of p-dichlorobenzene, and from 0.01 to 1% by weight of m-dichlorobenzene.

9. The process of claim 6 wherein the isomeric mixture of dichlorobenzenes contains from 10 to 30% by weight of o-dichlorobenzene, from 20 to 30% by weight of p-dichlorobenzene, and from 40 to 60% by weight of m-dichlorobenzene.

10. The process of claim 6 wherein the isomeric mixture of dichlorobenzenes contains from 0 to 3% by weight of o-dichlorobenzene, from 30 to 45% by weight of p-dichlorobenzene, and from 55 to 70% by weight of m-dichlorobenzene.

11. A process for the purification of p-dichlorobenzene and m-dichlorobenzene from an isomeric mixture of dichlorobenzenes which comprises
adding to the isomeric mixture of dichlorobenzenes an eutectic agent selected from the group consisting of 1,4-dibromobenzene, 1-bromo-4-chlorobenzene and a mixture of 1,4-dibromobenzene and 1-bromo-4-chlorobenzene,
heating the formed mixture to dissolve a part or the whole of the solid material,
cooling the mixture to a temperature lower than 30° C. and forming eutectic crystals consisting essentially of p-dichlorobenzene with the eutectic agent,
separating the eutectic crystals from the mixture,
heating the eutectic crystals and distilling purified p-dichlorobenzene and
distilling purified m-dichlorobenzene from the remaining mixture.

12. The process of claim 11 wherein 1-bromo-4-chlorobenzene is added to the isomeric mixture of dichlorobenzenes, and heated to form a mixture consisting essentially of about 36% by weight of m-dichlorobenzene, about 20% by weight of p-dichloro-benzene, and about 45% by weight of 1-bromodichlorobenzene, the formed mixture is cooled to between about −10° to about 5° C., and p-dichloro- of 99% purity is distilled at about 174.1° C. from the eutectic crystals that have been formed and separated.

13. The process of claim 12 wherein m-dichlorobenzene of 99.1% purity is distilled at about 173.0° C. from the remaining mixture.

14. The process of claim 11 wherein the p-dichlorobenzene is distilled at about 174.1° C.

15. The process of claim 11 wherein the m-dichlorobenzene is distilled at about 173.0° C.

* * * * *